United States Patent [19]
Bailey

[11] Patent Number: 5,494,669
[45] Date of Patent: Feb. 27, 1996

[54] PREPARATION FOR AND METHOD OF TREATING PSEUDOFOLLICULITIS BARBAE

[76] Inventor: Byron H. Bailey, 3508 24th St. NE., Washington, D.C. 20018

[21] Appl. No.: 300,519

[22] Filed: Sep. 6, 1994

Related U.S. Application Data

[63] Continuation of Ser. No. 73,037, Jun. 8, 1993, abandoned.
[51] Int. Cl.$^6$ ................................................ A61K 35/78
[52] U.S. Cl. .................... 424/195.1; 424/401; 424/73; 424/74
[58] Field of Search ................... 424/195.1, 401, 424/405, 73, 74; 514/887

[56] References Cited

U.S. PATENT DOCUMENTS

| | | | |
|---|---|---|---|
| 4,582,706 | 4/1986 | Bailey | 424/195.1 |
| 4,944,939 | 7/1990 | Moore | 424/73 |
| 5,034,221 | 7/1991 | Rosen et al. | 424/73 |
| 5,252,331 | 10/1993 | Curtis et al. | 424/401 |

*Primary Examiner*—Thurman K. Page
*Assistant Examiner*—Neil Levy
*Attorney, Agent, or Firm*—Theodore C. Miller; Alfred F. Hoyte, Jr.

[57] ABSTRACT

A preparation for and method of treating PFB. The preparation is a topical solution comprising a mixture of alophatic alcohol, liquid aloe, liquid camphor, and the soluble materials of the fresh fig leaves of *Ficus Carica*.

2 Claims, No Drawings

PREPARATION FOR AND METHOD OF TREATING PSEUDOFOLLICULITIS BARBAE

CROSS REFERENCE TO RELATED APPLICATION

This application is a continuation of application Ser. No. 08/073,037 filed Jun. 8, 1993 and now abandoned.

BACKGROUND OF THE INVENTION

The present invention relates to a skin disorder known as *pseudofolliculitis barbae* (PFB), and more particularly to a preparation for amd method of treating PFB.

PFB (commonly referred to as razor bumps) is a skin disorder which is caused by ingrown hairs which occur after shaving. The ingrown hairs cause painful inflammation which is sometimes accompanyied by infection which leaves the beard areas of the face covered with unsightly lesions.

Attempts have been made in the prior art to solve the problem. U.S. Pat. No. 5,034,221 issued to Rosen et al. describes a topical agent for treating PFB. Rosen discloses a combination of acetylsalicylic acid, corn starch, isopropyl alcohol, and aloe vera. The combination results in a preparation having a lotion like consistency. U.S. Pat. No. 4,944,939 issued to Moore discloses a preparation for the treatment of PFB. There are several embodiments, all of which have a lotion like or wax like consistency.

The problem with the prior art preparations lies in their consistency. The lotion like consistency makes the preparation difficult to dissolve completely into the skin and therefore tends to take a long time to apply. Rosen, for instance, describes a method for applying the preparation including two drying steps, one step where the excess is removed, and yet another step where an after-shave product is recommended to "render the coating of lotion of the product nearly invisible" (emphasis added). The problem is amplified when the preparation is applied to a beard or stubble since the lotion will tend to cling to the hair. Another problem with a preparation having a lotion like or wax like consistency is that it tends to stain shirt collars. This problem is particularly acute since a large percentage of men who shave daily also have to wear ties which exacerbates the problem since the collar button must be closed. Finally, to be effective, most of the preparations are applied overnight and tend to rub off on pillow cases thereby not only staining them but also resulting in a somewhat reduced effectiveness since some of the product is rubbed off.

SUMMARY OF THE INVENTION

The present invention is a preparation for and method of treating PFB. The preparation is a topical solution comprising a mixture of aliphatic alcohol, liquid aloe, liquid camphor, and the soluble materials of the fresh fig leaves of *Ficus Carica*.

It is an object of this invention to provide a product and method for the treatment of PFB.

It is another object of the present invention to provide a solution which has a liquid or after-shave like consistency and can be used in the treatment of PFB.

It is another object of the present invention to provide a preparation for the treatment of PFB which does not have to be rubbed into the skin.

It is yet another object of the present invention to provide a method for the treatment of PFB which method results in a reduced occurrence of lesions associated with PFB.

It is a further object of the present invention to provide a preparation for the treatment of PFB which is effective to reduce inflammation associated with PFB.

It is a still further object of the present invention to provide a preparation for the treatment of PFB which is effective to reduce the discomfort associated with PFB.

The above and yet other objects and advantages of the present invention will become apparent in the hereinafter set forth detailed description of the invention and claims appended herewith.

DETAILED DESCRIPTION OF THE INVENTION

The present inventive preparation consists in preferred embodiments of essentially a mixture of the following volumetric proportions:

160 oz. alcohol (isopropyl)
20 oz. aloe vera
1 oz. liquid camphor
20 average size nature fresh fig leaves of Calimyrna variety The mixture is prepared by introducing the alcohol into a crock or mixing bowl of adequate size, and adding the aloe to form a binary solution. Liquid camphor is added gradually up to the point to avoid turbidity, but in sufficient amounts to obtain a ternary solution. These amounts are 20 ounces of aloe vera and 1 ounce of liquid camphor per 160 ounces of the alcohol. Twenty fresh fig leaves are immersed in the solution, and stirred vigorously for 2 to 3 minutes, and the admixture is allowed to stand at room temperature (68 degrees F.) for at least 48 hours. The solution is decanted-off and then bottled.

The alcohol is added to reduce the incidence of infection which occurs with the lesions associated with PFB. While isopropyl alcohol represents the preferred aliphatic alcohol in the context of the invention, it is not critical, and any alcohol having up to and including six carbon atoms will suffice; thus methyl, ethyl, n-propyl, isopropyl, butyl, amyl and hexyl are equally useful as a component in the binary solution.

Aloe vera is added to reduce the inflammation associated with PFB caused lesions and also to provide a soothing effect.

Aloe vera in the approximate amount of ⅛th by volume of said alcohol is the preferred amount; however this too is not critical. The important consideration is that the amount of aloe be miscible with the alcohol so as to maintain a binary solution.

*Ficus Carica* is also added to reduce inflammation.

Any of the fresh fig leaves from *Ficus Carica*, to include most specifically, the Kadota, Black Mission, Calimyrna and Caprifig will suffice, however, the Calimyrna is the most preferred and in the amount of approximately 20 average size leaves.

Liquid Camphor is added as another soothing agent to reduce the temporary discomfort caused by the alcohol.

The directions for the use of the preparation are as follows:

1. Wash the face in a gentle manner (i.e. without scrubbing), and pat dry. It is recommended that a hypoallergenic fragrance free cleanser or soap be used.

2. Shave using downward strokes going in the direction of hair growth, pressing only firmly enough to remove the hair to a point just above the skin level. Shaving should be performed daily.

What is claimed is:

1. A preparation consisting of in volumetric proportion a ternary solution of about 160 ounces of an aliphatic alcohol having up to six carbon atoms, about 20 ounces of liquid aloe vera, and about 1 ounce of liquid camphor, and the materials soluble in said ternary solution at room temperature from about 20 average size mature fresh fig leaves of *ficus carica*.

2. The preparation described in claim 1 wherein the aliphatic alcohol is isopropyl alcohol.

* * * * *

UNITED STATES PATENT AND TRADEMARK OFFICE
CERTIFICATE OF CORRECTION

PATENT NO. : 5,494,669  Page 1 of 2
DATED : February 27, 1996
INVENTOR(S) : Byron H. Bailey It is certified that error appears in the above-identified patent and that said Letters Patent is hereby corrected as shown below:

Column 1, first line of the title, delete "AND METHOD OF".

Column 1, line 39, amend "nearly" to read --nearly--.

Column 2, line 26, delete "nature".

Column 3, between line 4 and line 5, insert the following:
--3. After shaving, splash product on the beard area.
4. Allow to dry naturally for about two to three minutes.
5. Avoid the use of after shaves or other fragrant solutions on the beard area.
6. Apply as an overnight preparation in accordance with steps 1, 3, and 4.

The inventive formulation has been tested on a very limited basis but the results have been most favorable.

While the invention has been described in specific terms, it is to be understood that minor changes in the preparation proportions are possible without departing from the spirit or scope of the invention as defined by the claims hereinafter set forth.--

UNITED STATES PATENT AND TRADEMARK OFFICE
CERTIFICATE OF CORRECTION

PATENT NO. : 5,494,669
DATED : February 27, 1996
INVENTOR(S) : Byron H. Bailey

It is certified that error appears in the above-indentified patent and that said Letters Patent is hereby corrected as shown below:

COlumn 4, line 3, claim 1, delete "mature".

Signed and Sealed this

Twenty-eighth Day of May, 1996

Attest:

BRUCE LEHMAN

*Attesting Officer*  *Commissioner of Patents and Trademarks*